(12) United States Patent
Smith

(10) Patent No.: US 6,372,769 B1
(45) Date of Patent: Apr. 16, 2002

(54) 5-CARBOXANILIDO-2,4-BIS-TRIFLUOROMETHYLTHIAZOLES AND THEIR USE TO CONTROL RICE BLAST

(75) Inventor: Frisby Davis Smith, North Wales, PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/730,017

(22) Filed: Dec. 5, 2000

Related U.S. Application Data

(60) Provisional application No. 60/171,242, filed on Dec. 16, 1999.

(51) Int. Cl.[7] ............... C07D 277/56; A01N 43/78
(52) U.S. Cl. ............... 514/365; 514/371; 548/200
(58) Field of Search ............... 514/371, 365; 548/200

(56) References Cited

U.S. PATENT DOCUMENTS 5,045,554 A * 9/1991 Art et al. ............... 514/365

FOREIGN PATENT DOCUMENTS

| EP | 0371950 A2 | 6/1990 |
|---|---|---|
| EP | 0371950 A3 | 6/1990 |
| EP | 0846416 A1 | 6/1998 |

* cited by examiner

*Primary Examiner*—Floyd D. Higel
*Assistant Examiner*—Kamal Saeed
(74) *Attorney, Agent, or Firm*—Thomas D. Rogerson

(57) ABSTRACT

The present invention provides 5-carboxanilido-2,4-bis-trifluoromethylthiazoles and their compositions. The compounds and compositions are effective for controlling fungal diseases on plants. They are particularly effective for controlling rice blast.

3 Claims, No Drawings

5-CARBOXANILIDO-2,4-BIS-TRIFLUOROMETHYLTHIAZOLES AND THEIR USE TO CONTROL RICE BLAST

This application claims benefit of provisional application No. 60/171,242 filed on Dec. 16, 1999.

The present invention relates to certain 5-carboxanilido-2,4-bis-trifluoromethylthiazoles and their use for controlling rice blast.

U.S. Pat. No. 5,045,554 discloses a class of substituted 5-carboxanilido-thiazoles useful for control of plant fungus disease such as, for example Basidiomycetes such as Rhizoctonia, Sclerotium, and Corticium, as well as Alternaria and Spirothica, when applied to the growing plant, preferably as a foliar spray. Such 5-carboxanilidothiazoles are not known to have significant activity against the organism causing rice blast (*Pyricularia oryzae*). We have discovered that certain of these 5-carboxanilidothiazoles, specifically those in which the thiazole ring is substituted with trifluoromethyl groups at the 2 and 4 positions, are surprisingly effective for control of rice blast. In addition, these compounds provide improved activity against a variety of other fungi when compared with similar compounds which do not contain the bis-trifluoromethyl substituted thiazole entity.

The present invention provides compounds of Formula I:

I 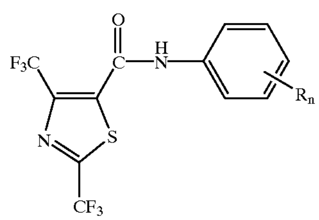 and salts thereof;

wherein: each R is independently halo (preferably chloro, bromo, or iodo), halo($C_1$–$C_5$)alkyl (preferably halo ($C_1$–$C_2$)alkyl, more preferably perhalomethyl, most preferably trifluoromethyl), halo($C_1$–$C_5$)alkoxy (preferably halo($C_1$–$C_2$)alkoxy, more preferably perhalomethoxy, most preferably trifluoromethoxy), nitro, cyano, pentahalosulfur (preferably pentafluorosulfur), halomethylthio, haloethylthio, ($C_1$–$C_2$)alkylsulfinyl, halo($C_1$–$C_2$)alkylsulfinyl, ($C_1$–$C_2$)alkylsulfonyl, or halo($C_1$–$C_2$)alkylsulfonyl; n is from two to five (preferably two to four, more preferably three to four, most preferably three). Salts of the compound of Formula I include salts of strong bases, preferably a salt from reaction with sodium or potassium hydroxide, diazabicycloundecene, or diazabicyclononane, more preferably a salt formed from reaction with sodium or potassium hydroxide. Preferably each R is independently halo, haloalkyl, or haloalkoxy. Preferably, at least one, more preferably at least two, of the R groups are located in the ortho and/or para positions. The compounds of this invention to not include compounds in which $R_n$ has the following substituent patterns: 2,4,6-trichloro, 2,3,4,5,6-pentachloro, 2,4,6-tribromo, 2,3,4,5,6-pentafluoro, and 2,6-dibromo-4-trifluoromethoxy.

The term “carboxanilido” means $C_6H_5$—NH—CO—. The term “alkyl” means straight or branched chain ($C_1$–$C_5$) alkyl, unless otherwise specified. The term “lipophilic” means having an affinity for organic solvents rather than aqueous solvents. The term “active ingredient” means a compound of Formula I and/or any other compound with pesticidal activity.

As used herein, all percentages are percent by weight, unless otherwise specified. All percentage ranges are inclusive and combinable. All ratios are by weight and all ratio ranges are inclusive and combinable.

A second embodiment of this invention provides compositions comprising one or more compounds of Formula I and an agronomically acceptable carrier. Another embodiment this invention provides a method to control fungal disease on a plant comprising applying to the plant, vegetative propagules of the plant including seeds and seedlings, the growing medium of the plant, or water around the plant foliage, a fungicidally effective amount of a composition comprising one or more compounds of Formula I, as described above.

The compounds and compositions of the present invention are particularly useful for the control of rice blast. However, they also control other phytopathogenic fungi on a wide variety of crops. The compositions may be applied as a seed protectant, as a seedling or seedling box treatment, as a foliar fungicide, as a soil fungicide, or as a combination thereof The quantity of the compound or composition required for control of a particular spectrum of fungi will depend upon the growth stage of the crop, the crop to be treated, the relative stage of infection by the fungi, the type and condition of soil, the amount of rainfall, and the specific compounds employed. Under some conditions the compounds or compositions of the invention may be incorporated into the soil or other growth medium prior to planting a crop. This incorporation may be by any convenient means, including mixing with the soil, applying the compositions to the surface of the soil and then discing or dragging into the soil to the desired depth, or by employing a liquid carrier. The compositions of this invention can be diluted or applied as is to plant foliage and/or soil as aqueous sprays by methods commonly employed, such as conventional high-volume hydraulic a sprays, low-volume sprays, air-blast, and aerial sprays. The dilution and rate of application will depend upon the type of equipment employed, the method and frequency of application desired, the fungicide application rate, and the fungi to be controlled. The compositions can be mixed with fertilizers or fertilizing materials before their application. The compositions can be utilized as the sole pesticidal agent or they can be employed in conjunction with other pesticidal agents such as, for example, microbicides, other fungicides, herbicides, insecticides, and acaricides.

In foliar applications an application rate of from 10 to 500 grams per hectare (“g/ha”), preferably from 30 to 250 g/ha, is usually employed. In soil applications an application rate of from 10 to 1000 g/ha, preferably from 100 to 500 g/ha, is usually employed.

For such purposes these compounds can be used in the technical grade or pure form as prepared or, preferably, as formulated compositions. Solid compositions include, for example: wettable powders typically containing, for example, from 10 to 90%, preferably from 50 to 90% active ingredient, from 2 to 10% dispersing agents, up to 10% stabilizers and/or other additives such as penetrants, stickers, and surfactants, and a solid inert carrier such as clay, silica, or natural or synthetic carrier; dusts which are usually formulated as a concentrate having a composition similar to a wettable powder but without dispersant and usually containing from 0.5 to 10% active ingredient; and granules containing, for example, from 0.01 to 80% active ingredient and 0 to 10% additives such as stabilizers, surfactants, slow release modifiers, and binding agents which are prepared by, for example, agglomeration or impregnation techniques and have a size greater than wettable powders and up to 1–2 millimeters. Liquid compositions include, for example, aqueous or solvent based solutions, emulsifiable concentrates, emulsions, suspension concentrates, and flowables which typically contain from 0.01 to 99.9% of the active ingredient, an agronomically acceptable carrier, and one or more adjuvants. More typically such liquid compositions will contain from 1.0 to 85% of the active ingredient.

As used herein, the term "agronomically acceptable carrier" means any material with which a compound of Formula I is formulated to facilitate application or to facilitate storage, transport, or handling of the compound of Formula I and which is not phytotoxic to plant foliage. A carrier may be a solid or liquid, including a material which is normally gaseous but which has been compressed to form a liquid. Any of the carriers typically useable in formulating fungicidal compositions may be used. Suitable solid carriers include, for example, natural and synthetic clays and silicates, salts such as calcium carbonate and ammonium sulfate, carbon-based materials such as charcoal and bitumen, sulfur, natural and synthetic resins, waxes, agar, fertilizers, cellulose-based materials such as sawdust and corn cobs, and mixtures thereof. Suitable liquid carriers include, for example, water, alcohols, ketones, ethers, aromatic and aliphatic hydrocarbons, petroleum fractions, chlorinated hydrocarbons, polar organic liquids, and mixtures thereof. Combinations of solid and liquid carriers may also be used.

It is usually desirable, particularly in the case of sprayable formulations, to include one or more adjuvants, such as wetting agents, spreading agents, dispersing agents, stickers, adhesives, emulsifying agents and the like in accordance with agricultural practices. Such adjuvants commonly used in the art can be found in *McCutcheon's Emulsifiers and Detergents, McCutcheon's Emulsifiers and Detergents/Functional Materials*, and *McCutcheon's Functional Materials* all published annually by McCutcheon Division of MC Publishing Company (New Jersey) and *Farm Chemicals Handbook* published by Meister Publishing Company (Ohio).

The fungicidal compositions of this invention may also contain other ingredients, for example, further active compounds possessing herbicidal, insecticidal, or fungicidal properties, in accordance with the requirements of the locus to be treated and the treatment method.

Compounds of Formula I are prepared by standard procedures as disclosed in U.S. Pat. No. 5,045,554 (see particularly columns 4–15) by reacting a 2,4-bis-trifluoromethyl substituted thiazole having a 5-carbonylchloride substituent with an appropriately substituted aniline in suitable solvent(s) at an elevated temperatures. An example process is as follows:

Preparation of 2,4-bis-trifluoromethylthiazole-5-carboxylic Acid Chloride

Step 1—Preparation of trifluorothioacetamide:

To a 1L 4-neck round bottom flask (RBF), equipped with a mechanical stirrer, nitrogen inlet, addition funnel and thermometer, was charged trifluoroacetamide (56.0 grams (g), 1.0 equiv. 0.495 mole) and 100 g of Lawesson's reagent followed by 500 milliliters (mL) of tetrahydrofuran. The reaction mixture was heated to boiling for 2 hours. The solvent was carefully removed by rotary evaporation to yield 86 g of crude product. This material was distilled by kugelrohr distillation under high vacuum (<1 mm Hg) to afford 54 g of light yellow liquid trifluorothioacetamide (84% yield).

Step 2—Preparation of ethyl chlorotrifluoroacetoacetate:

To a 500 mL 3-neck RBF equipped with a magnetic stirrer, nitrogen inlet, thermometer and gas bubbler was charged 200 g of ethyl trifluoroacetoacetate. Using an acetone/ice bath the reaction vessel was cooled to 0–10° C. and at this temperature chlorine gas was added to the reaction vessel via a gas bubbler at sufficient rate to maintain the reaction from 5 to 15° C. Chlorine gas was added until a yellow color persisted in the reaction mixture. The reaction solution was allowed to warm to room temperature and then heated to 30° C. while gas was evolved. When the gas evolution stopped, the resulting mixture provided 226 g of product (95% yield).

Step 3—Preparation of ethyl 2,4-bis-trifluoromethyl-5-thiazole carboxylate:

To a 3L 4-neck RBF equipped with a mechanical stirrer, reflux condenser, thermometer and addition funnel was charged 358 g of ethyl chlorotrifluoroacetoacetate (1.64 moles), 2,2,2-trifluorothioacetamide and 1000 mL of acetonitrile. To this mixture was added 331.9 g of triethylamine (2.0 eq, 3.28 moles) dropwise over 2.5 hours. During the addition the temperature was maintained at 30–38° C. and upon completion of the addition the reaction was heated to reflux for 2 hours and stirred overnight at room temperature. The reaction mixture was filtered and the resulting filtrate was concentrated by rotary evaporation to provide an oily solid which was dissolved in 1500 mL of ethyl acetate. This was washed with 2×500 mL of water, 1×500 mL of brine and concentrated by rotary evaporation to yield 356.6 g of ethyl 2,4-bis-trifluoromethyl-5-thiazole carboxylate which was purified by distillation.

Step 4—Preparation of 2,4-bis-trifluoromethylthiazole-5-carboxylic acid:

To a 1L 4-neck RBF was charged ethyl 2,4-bis-trifluoromethyl-5-thiazole carboxylate (23.8 g, 1.0 equiv., 81.2 mmole) in 100 mL THF and 50 mL water. The reaction mixture was cooled to 20° C. and 10% NaOH solution (32.5 g, 1.0 equiv., 81.2 mmole) was added. The ice-bath was removed after 5 minutes and the mixture was stirred for 4 hours. After reaction was complete, as determined by thin layer chromatography, 100 mL ether and 100 mL water were added. The aqueous phase was separated and acidified with conc. HCl, extracted with ether, and the ether was removed by rotary evaporation to give a solid which was washed with water and vacuum filtered. The solid was dried in a vacuum oven to give 16.5 g (76.7% yield) product as a brown solid, mp=98–101° C.

Step 5—Preparation of 2,4-bis-trifluoromethylthiazole-5-carboxylic acid chloride:

To a 500 mL 1-neck RBF under $N_2$ was added 2,4-bis-trifluoromethyl-thiazole-5-carboxylic acid (31.5 g, 1.0 equiv., 0.119 moles) in 25 mL chloroform and 1 mL dimethylformamide (DMF). To this solution was added thionyl chloride (28.3 g, 2.0 equiv., 0.24 moles). The reaction was then heated at reflux for 6 hours. The reaction was cooled to room temperature and concentrated by rotary evaporation at 30° C. to remove solvent. Chloroform was added, 3×25 mL portions, concentrating by rotary evaporation each time, to give 29.8 g (88.4% yield) product as a brown oil.

Aniline Coupling Reactions

Prep. of Compound 1—N-(2,4,6-trichlorophenyl)-2,4-bis-trifluoromethylthiazole-5-carboxanilide:

To a 250 mL 1-neck RBF under nitrogen was added 2,4-bis-trifluoromethyl-thiazole-5-carboxylic acid chloride (25.8 g, 1.0 equiv., 91.0 mmoles) in 30 mL toluene and then 2,4,6-trichloroaniline (17.9 g, 1.0 equiv., 91.0 mmoles). The mixture was heated at reflux for 6 hours with monitoring by gas-liquid chromatography (GLC). Upon completion the reaction was cooled to room temperature. A dark colored solid formed upon cooling after residual toluene was evaporated. The dark colored solid was washed with methylene chloride, vacuum filtered, and further washed with hexanes to give 33.2 g (82.2% yield) product as an off-white solid, mp=180–182° C.

Preparation Compound 14—2'-bromo-4',6'-dichloro-2,4-bis-trifluoromethyl-1,3-thiazole-5-carboxanilide To a 125 mL 1-neck flask under nitrogen was added 1.0 g (1.0 eq., 3.5 mmole) of 2,4-bis-trifluoromethyl-1,3-thiazole-5-carboxylic acid chloride and 0.85 g (1.0 eq., 3.5 mmole) of 2-bromo-4,6-dichloroaniline in 10 mL toluene. The mixture was heated at reflux for 6 hours. The mixture was cooled and the solvent was removed leaving a solid residue. The residue was triturated with methylene chloride followed by a hexane wash to give 1.1 g product as a white/pink solid (mp=179–182° C., 63.9% yield) (NMR ($^1$H, 300 MHz: 7.5(d, 1H); 7.6(d, 1H); 7.7(s, 1H)).

Other compounds in the following table were prepared in a similar manner:

| Cmpd # | $R_n$ | Melting Point ° C. | NMR $^1$H, 300 MHz |
|---|---|---|---|
| 1 | 2,4,6-tri-Cl | 181–182 | 7.46 (s, 2H); 7.65 (s, 1H) |
| 2 | 2,3,4,5,6-penta-Cl | 230–231 | |
| 3 | 2,4,6-tri-Br | 204–205 | |
| 4 | 2,3,4,5-tetra-F | 113–115 | |
| 5 | 2,6-di-Br-4-OCF$_3$ | 167–168.5 | 7.57 (s, 2H); 7.7 (s, 1H) |
| 6 | 4-Br-2,6-di-Cl | 191–194 | 7.6 (s, 2H); 7.7 (s, 1H) |
| 7 | 3,4,5-tri-Cl | 179–182 | 7.7 (s, 2H); 7.9 (s, 1H) |
| 8 | 2,3,4-tri-Cl | 132–134 | 7.49 (m, 1H); 8.35 (m, 1H); 8.46 (s, 1H) |
| 9 | 2,4,5-tri-Cl | 153–155 | 7.55 (s, 1H); 8.4 (s, 1H); 8.64 (s, 1H) |
| 10 | 2,4-di-Cl | 122–125 | 7.35 (m, 1H); 7.47 (m, 1H); 8.37 (d, 2H) |
| 11 | 2,5-di-Cl | 142–144 | 7.17 (m, 1H); 7.39 (d, 1H); 8.48 (d, 2H) |
| 12 | 2,6-di-Cl | 181–183 | 7.29 (m, 1H); 7.44 (d, 2H); 7.7 (s, 1H) |
| 13 | 3,5-di-Cl | 175–178 | 7.26 (s, 1H); 7.53 (d, 2H); 7.9 (s, 1H) |
| 14 | 2-Br-4,6-di-Cl | 179–182 | 7.5 (d, 1H); 7.6 (d, 1H); 7.7 (s, 1H) |

Evaluation of Fungicidal Activity

Numerous compounds and compositions of this invention were tested for fungicidal activity in vivo against the plant diseases described below. The chemicals for testing were all technical material, >95% active ingredient. Each compound was compared with an identically aryl substituted analog except that rather than being a 2,4-bis-trifluoromethylthiazole, the comparison compound was a 2-methyl-4-trifluoromethylthiazole. The comparison compounds are designated "C-" in the following table. All compounds were first dissolved overnight in a 1:1 (v/v) mixture of acetone and methanol. The following morning, they were diluted with a 2:1:1 (v/v) mixture of water, acetone, and methanol, to achieve the appropriate concentrations, beginning at an application rate of 300 g/ha.

Test plants were grown under greenhouse conditions in a peat moss and vermiculite soil-less mix, except rice plants that were grown in 50% mix and 50% sterilized soil (v/v). All plants were planted in approx. 5 cm×5 cm plastic pots.

Each test solution was sprayed onto the plants and allowed to dry for two hours. Then the plants were inoculated with fungal spores. Each test utilized control plants which were sprayed with the solvent mixture and inoculated. For these protective tests, the plants inoculated with the two powdery mildews were inoculated the same day as spraying. All other inoculations were performed one day after spraying the plants with the compound. After spraying, the plants were stored at room temperature under low light until inoculation.

The remainder of the technique of each of the tests is given below along with the results for various compounds described herein. The results are percent disease control are compared to the untreated check, wherein one hundred was rated as complete disease control and zero as no disease control. The application of the fungal spores to the treated test plants to induce the following plant diseases was as follows:

Rice Blast ("RB")

Cultures of *Pyricularia oryzae* were maintained on potato dextrose agar (PDA) for two to three weeks. Spores of *P. oryzae* were removed from the PDA plates by flooding the plate surface with distilled water, amended with Tween™-80 surfactant (Fisher Scientific) at 1 drop per 100 mL distilled water. The upper surface of the fungal colony was scraped with a blunt instrument until most of the spores were released into the aqueous environment. After filtering the spore suspension through two layers of cheese cloth, the spore count was adjusted to $5 \times 10^5$ spores/mL.

The spore suspension was sprayed onto 12-day old rice plants, cultivar M-201, using a DeVilbiss atomizer. Each pot of rice plants, containing 20 to 30 plants, received approximately 1 mL of inoculum. The inoculated plants were placed in a dark humidity cabinet at 20° C. for 36 hours to allow for infection. After the infection period, the plants were placed in the greenhouse. After 6 more days, the plants were evaluated for percent disease control.

Cucumber Powdery Mildew ("CPM")

A culture of powdery mildew *Sphaerotheca fulginea* was maintained on large cucumber plants, cultivar Bush Champion, in the greenhouse. Inoculum was prepared by placing five to ten heavily mildewed leaves in a glass jar with 500 mL of water containing five drops of Tween™-80 surfactant. After shaking the liquid and leaves to release the spores, the suspension was filtered through cheesecloth, and the spore count was adjusted to 100,000 spores/mL.

The upper leaf surface of the plants was sprayed with the spore suspension just prior to runoff, using a hand-held pump spray bottle. The plants were maintained in the greenhouse for infection and disease development. Seven days after inoculation, the plants were evaluated for percent disease control.

Grape Downy Mildew ("GDM")

The fungal pathogen *Plasmopara viticola* was cultured on small grape plants derived from plant tissue culture from the cultivar Delaware. Infected leaves producing spores were collected and frozen, until the spores were needed. Treated plants were sprayed with a spore suspension in water, containing 200,000 spores/mL. The plants were placed in an unlit humidity cabinet at 20° C. for 24 hours. After that infection period, the plants were transferred to a growth chamber at 18° C. and 90% humidity to allow for disease development. The percent disease control was evaluated seven days after inoculation.

Septoria on Wheat ("SNW")

The fungal pathogen *Septoria nodorum* was cultured on Czapek-Dox-V8 agar in an incubator at 18° C., set to a 12-hr day night cycle. After 2 to 3 weeks, the plates were flooded with water, containing 1 drop of Tween™-80 per 100 mL water. The upper surface of the fungal colony was scraped with a blunt instrument until most of the spores were released into the water. The spore suspension was filtered though cheesecloth, and the spore count was adjusted to $2 \times 10^6$ spores per mL.

The spore suspension was sprayed onto chemically-treated wheat plants, 7-days old, cultivar Fielder. The plants were placed in a fluorescent-lighted mist chamber (12 hr light, 12 hr dark) for 5 days. After this time, the plants were moved to a growth chamber for 2 more days set to 24° C. at 80% humidity. The plants were then evaluated for percent disease control.

Wheat Powdery Mildew ("WPM")

The fungal pathogen *Erysiphe graminis* f. sp. tritici was cultured on wheat seedlings, cultivar Fielder, by inoculating 7-day old plants. After 8 days in a controlled temperature room at 18° C., the wheat powdery mildew spores were shaken directly from the culture plants onto 7-day old wheat seedlings which had been previously treated with experimental compounds. The inoculated seedlings were kept in a controlled temperature room at 18° C. and 80% humidity to allow for disease development. The percent disease control was evaluated seven days after inoculation.

Wheat Leaf Rust ("WLR")

The fungal pathogen *Puccinia recondita* f. sp. tritici was maintained by inoculating 7-day old wheat plants, cultivar Fielder. Approximately two-weeks later, spores were collected from the leaves by scraping the plants over aluminum foil to collect the spores. The spores were cleaned by sieving through a 250-micron size screen and stored dry. The dried spores were used within one month.

A spore suspension was prepared from dry uredia spores by adding 20 mg (9.5 million spores) per mL of Soltrol 170™ nonphytotoxic oil (Phillips Petroleum Co.). The suspension was dispensed into gelatin capsules (0.7 mL capacity) which attach to the oil atomizers. One capsule was used for twenty pots of wheat, each pot containing 20 to 30 plants of the cultivar Fielder that were 7-days old. After waiting for at least 15 minutes for the oil to evaporate from the wheat leaves, the plants were placed in a dark mist chamber at 20° C. for 24 hours. The plants were then placed in the greenhouse and evaluated after an additional 12 days for percent disease control.

The results of these evaluations are as follows:

| Cmpd # | 1 | C-1 | 2 | C-2 | 3 | C-3 | 4 | C-4 | 5 | C-5 |
|---|---|---|---|---|---|---|---|---|---|---|
| Rate (g/ha) and Disease | | | | | | | | | | |
| 300 RB | 95 | 0 | 85 | 50 | 90 | 0 | 50/5 | 80 | 95 | 0 |
| 75 | 95 | 0 | 85 | 0 | 85 | 0 | 0 | 0 | 95 | 0 |
| 19 | 85 | 0 | 80 | 0 | 80 | 0 | 0 | 0 | 90 | 0 |
| 5 | 50 | 0 | 0 | 0 | 50 | 0 | 0 | 0 | NT | 0 |
| 300 CPM | 100 | 95 | 99 | 95 | 99 | 80 | —/5 | 90 | 100/5 | 95 |
| 75 | 85 | 75 | 95 | 90 | 85 | 50 | 0/5 | 80 | 75/5 | 95 |
| 19 | 50 | 0 | 85 | 75 | 0 | 0 | 0 | 0 | 0 | 50 |
| 5 | 0 | 0 | 75 | 0 | 0 | 0 | 0 | 0 | NT | 0 |
| 300 GDM | 100 | 0 | 95 | 0 | 75 | 50 | 90 | 95 | 0 | 0 |
| 75 | 90 | 0 | 75 | 0 | 50 | 0 | 75 | 95 | 0 | 0 |
| 19 | 0 | 0 | 0 | 0 | 0 | 0 | 0 | 0 | 0 | 0 |
| 5 | 0 | 0 | 0 | 0 | 0 | 50 | 0 | 0 | NT | 0 |
| 300 SNW | 90 | 50 | 80 | 80 | 80 | 75 | —/5 | 50 | 80 | 85 |
| 75 | 80 | 50 | 75 | 50 | 75 | 50 | 75 | 0 | 75 | 0 |
| 19 | 0 | 0 | 50 | 0 | 50 | 50 | 0 | 0 | 75 | 0 |
| 5 | 0 | 0 | 0 | 0 | 0 | 0 | 0 | 0 | NT | 0 |
| 300 WPM | 99 | 50 | 80 | 0 | 85 | 50 | 75 | 75 | 95 | 75 |
| 75 | 85 | 0 | 80 | 0 | 80 | 0 | 0 | 50 | 95 | 75 |
| 19 | 75 | 0 | 75 | 0 | 50 | 0 | 0 | 0 | 80 | 50 |
| 5 | 0 | 0 | 50 | 0 | 50 | 0 | 0 | 0 | NT | 0 |
| 300 WLR | 100 | 99 | 100 | 90 | 99 | 95 | 90 | 100 | 100 | 100 |
| 75 | 100 | 99 | 99 | 90 | 99 | 90 | 0 | 90 | 100 | 100 |
| 19 | 95 | 95 | 100 | 85 | 90 | 80 | 0 | 50 | 95 | 100 |
| 5 | 50 | 50 | 90 | 75 | 85 | 75 | 0 | 50 | NT | 85 |

NT = not tested
— = death of plant
/5 = some necrosis of plant tissue making disease control assessment difficult.

These data indicate that the bis-trifluoromethylthiazole-substituted compounds generally provide improved activity when compared with identically substituted compounds without the bis-trifluoromethyl groups. This is particularly true for control of rice blast wherein all of the comparison compounds except one are inactive (i.e. 0 to 50% control) at the highest application rate tested.

I claim:

1. A method comprising controlling rice blast by applying a fungicidally effective amount of a composition comprising one or more compounds of the formula

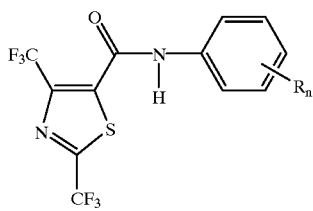

wherein n is 3;

each R is independently selected from the group consisting of halo, halo($C_1$–$C_5$) alkyl, halo($C_1$–$C_5$) alkoxy, nitro, cyano, pentahalosulfur, halomethylthio, ($C_1$–$C_2$) alkylsulfinyl, halo($C_1$–$C_2$)alkylsulfinyl, ($C_1$–$C_2$) alkylsulfonyl, or halo($C_1$–$C_2$)alkylsulfonyl; and said R's are at the 2,4, and 6 positions.

2. A method according to claim 1 wherein each R is independently selected from the group consisting of chloro, bromo, iodo, perhalomethyl, or perhalomethoxy.

3. A method according to claim 1 wherein each R is independently selected from the group consisting of chloro, bromo, or iodo.

* * * * *